United States Patent
Sugiyama et al.

(10) Patent No.: US 9,576,712 B2
(45) Date of Patent: Feb. 21, 2017

(54) MAGNETIC CIRCUIT FOR MAGNETIC FIELD GENERATOR

(71) Applicant: Hitachi Metals, Ltd., Tokyo (JP)

(72) Inventors: Eiji Sugiyama, Takasaki (JP); Masaaki Aoki, Takasaki (JP)

(73) Assignee: Hitachi Metals, Ltd., Tokyo (JP)

( * ) Notice: Subject to any disclaimer, the term of this patent is extended or adjusted under 35 U.S.C. 154(b) by 0 days.

(21) Appl. No.: 14/409,181

(22) PCT Filed: Jun. 26, 2013

(86) PCT No.: PCT/JP2013/067505
§ 371 (c)(1),
(2) Date: Dec. 18, 2014

(87) PCT Pub. No.: WO2014/007122
PCT Pub. Date: Jan. 9, 2014

(65) Prior Publication Data
US 2015/0137922 A1    May 21, 2015

(30) Foreign Application Priority Data

Jul. 2, 2012    (JP) .................................. 2012-148864

(51) Int. Cl.
*H01F 1/00*        (2006.01)
*H01F 7/02*        (2006.01)
(Continued)

(52) U.S. Cl.
CPC ............. *H01F 7/0205* (2013.01); *G01R 33/38* (2013.01); *G01R 33/383* (2013.01);
(Continued)

(58) Field of Classification Search
CPC ... G01R 33/3806; G01R 33/38; G01R 33/383; G01R 33/60; H01F 7/0205; G01N 24/10
(Continued)

(56) References Cited

U.S. PATENT DOCUMENTS 4,672,346 A  *  6/1987  Miyamoto et al. ........... 335/296
6,147,578 A     11/2000  Panfil et al.
(Continued)

FOREIGN PATENT DOCUMENTS

JP    S61-82607 U    5/1986
JP    2001-076925    3/2001
(Continued)

OTHER PUBLICATIONS

English Translation of International Search Report for PCT/JP2013/067505 mailed Sep. 24, 2013, 2 pages.
(Continued)

*Primary Examiner* — Bernard Rojas
(74) *Attorney, Agent, or Firm* — Rudy J. Ng; Bret E. Field; Bozicevic, Field & Francis LLP

(57) ABSTRACT

A magnetic circuit that forms an arc-shaped magnetic field space is provided. Of two magnets constituting a first magnetic circuit 10, a first magnetic pole 1 is provided with a first yoke 11 that is arc-shaped in planar view, a first magnet 13 that is arc-shaped in planar view and a magnetic pole piece 15. On the other hand, a second magnetic pole 2 is provided with a second yoke 21 that is arc-shaped in planar view, a second magnet 23 that is arc-shaped in planar view and a magnetic pole piece 25. The first magnetic pole piece 15 and the second magnetic pole piece 25 are disposed so as to be opposed to each other while being separated from each other. The first magnet 13 and the second magnet 23 are formed by arranging a plurality of small magnets.

12 Claims, 13 Drawing Sheets

(51) Int. Cl.
*G01R 33/38* (2006.01)
*G01R 33/383* (2006.01)
*G01N 24/10* (2006.01)
*G01R 33/60* (2006.01)
*G01R 33/3873* (2006.01)

(52) U.S. Cl.
CPC ......... *G01R 33/3806* (2013.01); *G01N 24/10* (2013.01); *G01R 33/3873* (2013.01); *G01R 33/60* (2013.01)

(58) Field of Classification Search
USPC .......................................... 335/286, 302–306
See application file for complete search history.

(56) References Cited

U.S. PATENT DOCUMENTS

| | | | | |
|---|---|---|---|---|
| 6,297,634 | B1* | 10/2001 | Aoki | .............................. 324/315 |
| 6,794,973 | B1* | 9/2004 | Aoki | ................. G01R 33/3806 335/216 |
| 7,796,002 | B2* | 9/2010 | Hashimoto | ........ G01R 33/3802 310/152 |
| 2005/0046533 | A1 | 3/2005 | Chell | |
| 2005/0092395 | A1* | 5/2005 | Aoki et al. | .................... 148/102 |
| 2005/0242912 | A1* | 11/2005 | Chell et al. | .................... 335/306 |
| 2009/0076324 | A1 | 3/2009 | Takayama et al. | |
| 2011/0112395 | A1 | 5/2011 | Ichikawa et al. | |

FOREIGN PATENT DOCUMENTS

| | | |
|---|---|---|
| JP | 2002-502648 | 1/2002 |
| JP | 2005-080963 A | 3/2005 |
| JP | 2006-204551 | 8/2006 |
| JP | 2010-227247 | 10/2010 |
| JP | 2011-527222 | 10/2011 |
| WO | WO0155732 A2 | 8/2001 |
| WO | WO2008007771 A1 | 1/2008 |
| WO | WO2011121435 A1 | 10/2011 |

OTHER PUBLICATIONS

Extended European Search Report for EP application No. 13812934.1 dated Apr. 20, 2016, 9 pages.

* cited by examiner

MAGNETIC CIRCUIT FOR MAGNETIC FIELD GENERATOR

This application is the national phase under 35 U.S.C. §371 of PCT International Application No. PCT/JP2013/067505 which has an International filing date of, Jun. 26, 2013 and designated the United States of America.

BACKGROUND

1. Field of the Invention

The present invention relates to a magnetic circuit that generates magnetic resonance in an object.

2. Description of the Related Art

Within a living body, reactive oxygen species are generated due to external factors such as radiation and ultraviolet rays or internal factors such as hypoxia and inflammation. Therefore, precisely measuring free radicals such as reactive oxygen species in the body are important for the people's health and welfare such as evaluation and creation of antioxidant medicines and the like.

Japanese Patent Application Laid-Open Publication No. 2006-204551 (Patent Document 1, hereinafter) describes a measurement instrument that performs a measurement necessary for obtaining information on free radicals within an animal body. In the measurement instrument, a first external magnetic field generation device for ESR (Electron Spin Resonance) excitation and a second external magnetic field generation device for MRI (Magnetic Resonance Imaging system) excitation apply a magnetic field to a coil that moves in a linear direction. The ESR is a method of obtaining information on free radicals within a living body accommodated in a coil by measuring a signal generated by electron spin resonance. On the other hand, the MRI is a method of obtaining information on the form of a living body by measuring a signal generated by nuclear magnetic resonance. Thereby, the measurement instrument supplements the functional information on free radicals obtained by the ESR with the information obtained by the MRI and obtains information on free radicals in the animal body. Moreover, the measurement instrument of Patent Document 1 is used also as a nuclear-electron multiple magnetic resonance measurement instrument that causes a transition of the electron spin in a living body by the Overhauser effect, causes an energy transition on the nuclear spin and displays a functional image and a morphological image of each part within the living body.

In addition, Japanese Patent Application Laid-Open Publication No. 2010-227247 (Patent Document 2, hereinafter) discloses a technology of applying a first magnetic field for ESR measurement and a second magnetic field for MRI measurement to a moving coil mounted on a rotary table.

In order for a measurement instrument to perform ESR measurement with high sensitivity, it is desired to apply a uniform magnetic field for a rather long time and sufficiently excite the electron spin in the living body. However, when the relaxation time after the electron spin excitation is considered, since it is more desirable to perform the MRI excitation at a short time interval after the ESR excitation, the rotation speed of the rotary table cannot be decreased. Therefore, since it is necessary that the uniform magnetic field space be large, a plurality of disk-shaped magnets are provided so as to be juxtaposed to each other in the first external magnetic field generation device.

SUMMARY

However, since the first external magnetic field generation device that excites the electron spin described in Patent Document 2 uses disk-shaped magnets, the uniform magnetic field space is limited to a space that is circular in planar view in the neighborhood of the center of each external magnetic field generation device. Therefore, there is a problem in that the uniform magnetic field space formed by the first external magnetic field generation device is still too small for sufficiently exciting the electron spin and for this reason, the time for which the first external magnetic field generation device applies a magnetic field is insufficient.

The present invention is made based on such a problem, and an object thereof is to provide a magnetic circuit capable of applying a magnetic field to an object for a sufficient time.

A magnetic circuit according to the present invention is characterized by being provided with two arc-shaped magnets disposed so as to be opposed to each other and two arc-shaped yokes disposed so as to be opposed to each other in the same direction as the two magnets with the two magnets interposed between the yokes.

According to the present invention, since the magnets are arc-shaped, the magnetic field can be applied to the object for a sufficient time.

The magnetic circuit according to the present invention is characterized in that the two magnets are formed by arranging a plurality of small magnets along a large diameter side arc portion, a small diameter side arc portion and coupling portions coupling ends of the two arc portions.

According to the present invention, since the magnets are formed so as to include the large diameter side arc portion, the small diameter side arc portion and coupling portions coupling the ends of the two arc portions, the magnetic field can be made uniform in a large space.

The magnetic circuit according to the present invention is characterized by being provided with two arc-shaped magnetic pole pieces disposed between the two magnets in the same direction as the two magnets and a one or more protruding pieces provided on an outer rims of each of the magnetic pole pieces and protruding toward the other magnetic pole piece.

According to the present invention, since the magnets are arc-shaped, the magnetic field can be applied to the object for a sufficient time.

The magnetic circuit according to the present invention is characterized in that the protruding pieces includes one or more large diameter side protruding pieces located on a large diameter side of the magnetic pole piece(s) and one or more small diameter side protruding pieces located on a small diameter side of the magnetic pole piece(s).

According to the present invention, since the protruding pieces are provided to the magnetic pole piece(s), the magnetic field can be made uniform in a large space.

The magnetic circuit according to the present invention is characterized in that the yokes include a plurality of hole portions along a similar arc similar to outer rims of the magnets.

According to the present invention, the magnetic field strength can be partly adjusted by, for example, screwing screw(s) in the hole portion(s) as appropriate.

The magnetic circuit according to the present invention is characterized by being provided with a plate-like auxiliary yoke that couples the two yokes.

According to the present invention, the magnetic flux can be effectively used by providing the auxiliary yoke.

The magnetic circuit according to the present invention is characterized in that the auxiliary yoke is provided along outer rims on the large diameter side of the two yokes and one end side in a direction of a length is thicker than other end side.

According to the present invention, by making the one end side of the auxiliary yoke in the direction of the length thicker than the other end side, when another magnetic circuit is provided on the one end side, the influence of the magnetic field leaking from the above-described another magnetic circuit can be suppressed.

The magnetic circuit according to the present invention is characterized by being provided with one or more auxiliary magnets attached to the magnets.

According to the present invention, the magnetic field strength can be partly adjusted by providing one or more auxiliary magnets.

The magnetic circuit according to the present invention is characterized in that one or more auxiliary magnets are fixed to the one end side which is an inside of one or more coupling portions.

According to the present invention, when another magnetic circuit is provided on the one end side, the influence of the magnetic field leaking from the above-described another magnetic circuit can be suppressed by fixing the auxiliary magnet to the one end side which is the inside of the coupling arc portion.

The magnetic circuit according to the present invention is characterized in that a non-magnetic plate is disposed between the magnets and the yokes opposed to the magnets.

According to the present invention, the magnetic field strength of the entire magnetic circuit can be adjusted by the non-magnetic plate.

According to the present invention, since the magnets constituting the magnetic circuit are arc-shaped, the magnetic field can be applied to the object to be measured for a sufficient time.

DETAILED DESCRIPTION

First Embodiment

Figure 1:
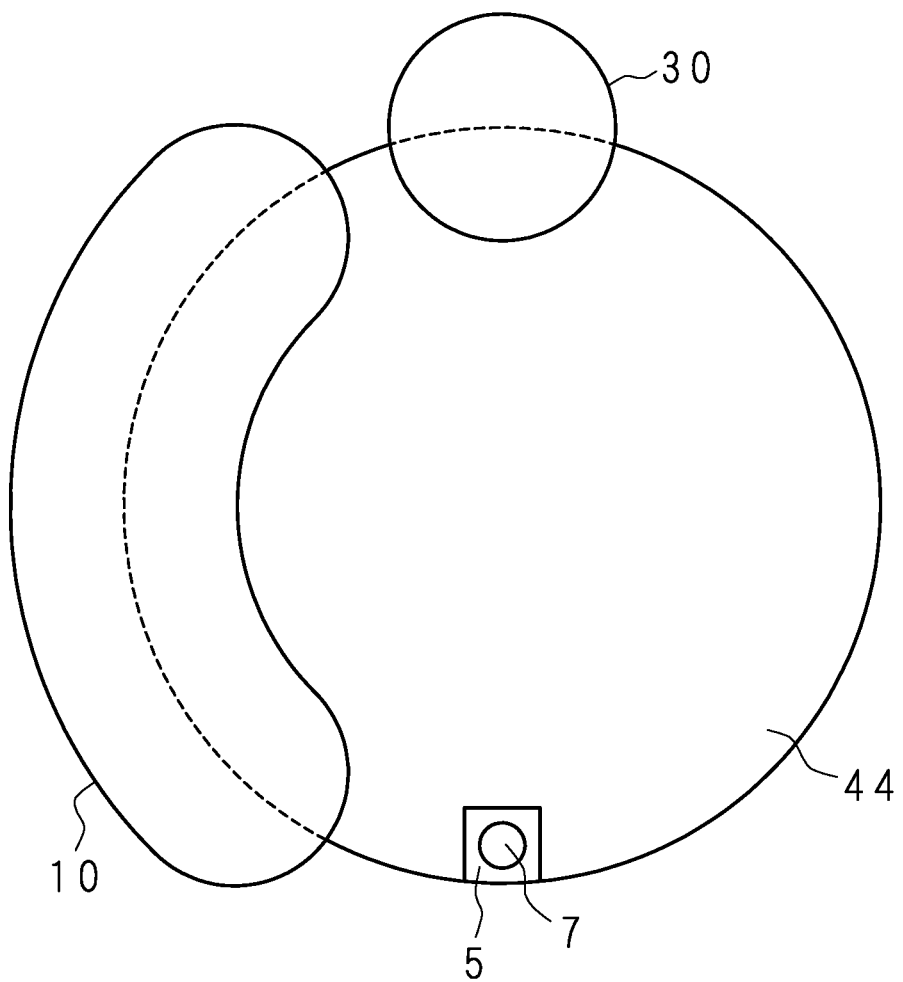
FIG. 1 is a schematic plan view showing a magnetic field application device.
Figure 2:
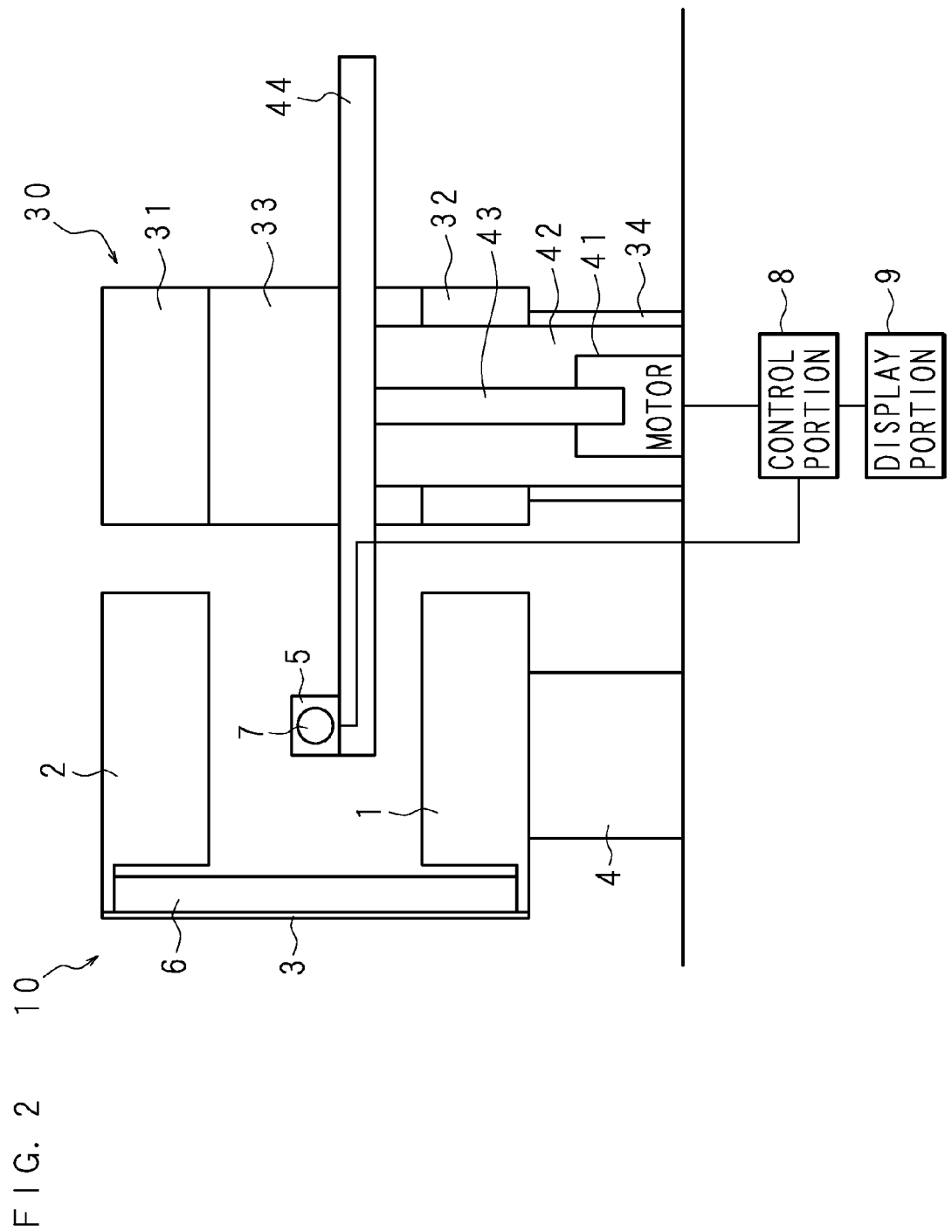
FIG. 2 is a schematic side view showing the magnetic field application device.

The first embodiment of the present invention will be described. FIG. 1 and FIG. 2 are a schematic plan view and a schematic side view of a magnetic field application device. The magnetic field application device includes a coil 5, a motor 41, a device stand 42, a rotation shaft 43, a rotary stand 44, a first magnetic circuit 10 and a second magnetic circuit 30. The first magnetic circuit 10 includes a first magnetic pole 1, a second magnetic pole 2, a back yoke 3 as a third yoke, a mounting stand 4 and a support pillar 6. The second magnetic circuit 30 includes magnetic poles 31 and 32, a back yoke 33 and a mounting stand 34.

The device stand 42 in the rotary device is cylindrical, and the motor 41 is embedded therein. From the device stand 42, the rotation shaft 43 extending in the vertical direction protrudes. On the upper end of the rotation shaft 43, the rotary stand 44 that is disk-shaped and coaxially fixed to the rotation shaft 43 is provided. By the motor 41 being activated, the rotation shaft 43 rotates clockwise. A control portion 8 which is connected to the motor 41 controls the activation and stopping of the motor 41 and obtains information on the rotation angle of the rotation shaft 43.

On the rim of the upper surface of the rotary stand 44, the coil 5 which is cylindrical is fixed in a horizontally-long orientation. The coil 5 is hollow, and a living body 7 such as a mouse or a rat as the object to be measured is accommodated therein. The living body 7 is an example; for example, a semiconductor device or the like may be the object to be measured in order to analyze the structure or the function. The coil 5 is connected to the control portion 8, and the control portion 8 transmits a signal of a predetermined frequency to the coil 5. When electron spin resonance occurs in the living body 7, an electron spin resonance signal is generated. When nuclear magnetic resonance occurs in the living body 7, a nuclear magnetic resonance signal is generated. The coil 5 detects such an electron spin resonance signal and a nuclear magnetic resonance signal, and transmits them to the control portion 8. The control portion 8 images the electron spin resonance signal and the nuclear magnetic resonance signal and displays them on a display portion 9. The display portion 9 is, for example, a liquid crystal display, a plasma display or an organic EL (Electro Luminescence) display.

The first magnetic circuit 10 is used as an electron spin excitation device or the like, for example, in the ESR or the OMRI (Overhauser Magnetic Resonance Imaging system). The first magnetic pole 1 in the first magnetic circuit 10 is arc-shaped in planar view along the outer rim of the rotary stand 44, and is mounted on the mounting stand 4. The second magnetic pole 2 has a shape plane-symmetric with the first magnetic pole 1 and is disposed so as to be opposed to the first magnetic pole 1 in the vertical direction with a gap in between. In the following, the direction from the first magnetic pole 1 toward the second magnetic pole 2 is the upward direction. However, such a direction is an example and the present invention is not limited thereto. Therefore, the first magnetic pole 1 and the second magnetic pole 2 are not necessarily arc-shaped in planar view as long as they are arc-shaped.

The first magnetic pole 1 and the second magnetic pole 2 are coupled together through the back yoke 3 provided in order that a later-described first yoke 11 and second yoke 21 that the first magnetic pole 1 and the second magnetic pole 2 are provided with, respectively, effectively use the magnetic flux. The second magnetic pole 2 is supported by the support pillar 6 provided along the back yoke 3. The first magnetic pole 1 and the second magnetic pole 2 generate a magnetic field in the gap. The rotary stand 44 is disposed so that part thereof passes through the gap between the first magnetic pole 1 and the second magnetic pole 2. By the rotary stand 44 rotating about the rotation shaft 43, the coil 5 passes through the gap.

In a position separated from the first magnetic circuit 10 in a clockwise direction along the outer rim of the rotary stand 44, the second magnetic circuit 30 is provided. The second magnetic circuit 30 is used as a nuclear spin excitation device or the like in the MRI, the OMRI or the like. In the second magnetic circuit 30, the two magnetic poles 31 and 32 having disk-shaped magnets are disposed so as to be opposed to each other with a gap in between. Thereby, the second magnetic circuit 30 generates a magnetic field in the gap. By the rotation shaft 43 rotating, the coil 5 passes through the gap between the magnetic pole 31 and the magnetic pole 32.

The operation of the magnetic field application device will be described. A probe agent which is a derivatized nitroxyl radical sensitive to redox metabolism in the living body is injected in the living body 7. The control portion 8 transmits a signal indicating the start of the operation, to the motor 41. The motor 41 receives the signal from the control portion 8, and rotates the rotation shaft 43. The rotation speed is, for example, one rotation per second. The numerical values shown in the present embodiment are examples and the present invention is not limited thereto.

The control portion 8 transmits a signal of a predetermined frequency that generates electron spin resonance, to the coil 5 immediately before the coil 5 enters the gap in the first magnetic circuit 10 based on the information on the rotation angle of the rotation shaft 43. By the coil 5 receiving the signal of the predetermined frequency and passing through the first magnetic circuit 10, a magnetic field is applied to the coil 5 and electron spin resonance occurs in the living body 7. The coil 5 detects an electron spin resonance signal generated by the electron spin resonance in the living body 7. The control portion 8 receives the electron spin resonance signal detected by the coil 5.

The control portion 8 stops the transmission of the signal of the predetermined frequency that generates electron spin resonance, at the point of time when the coil 5 finishes passing through the gap in the first magnetic circuit 10. Moreover, the control portion 8 transmits a signal of a predetermined frequency that generates nuclear magnetic resonance, to the coil 5 immediately before the coil 5 enters the gap in the second magnetic circuit 30.

By the coil 5 receiving the signal of the predetermined frequency and passing through the gap in the second magnetic circuit 30, a magnetic field is applied to the coil 5 and nuclear magnetic resonance occurs in the living body 7. The coil 5 detects a nuclear magnetic resonance signal generated by the nuclear magnetic resonance. The control portion 8 receives the nuclear magnetic resonance signal detected by the coil 5. The control portion 8 stops the transmission of the signal of the predetermined frequency that generates nuclear magnetic resonance, at the point of time when the coil 5 finishes passing through the gap in the second magnetic circuit 30. The control portion 8 transmits a signal indicating the stop of the operation, to the motor 41. The motor 41 receives the signal from the control portion 8, and stops the rotation of the rotation shaft 43.

The control portion 8 performs the processing of imaging free radicals of the living body 7 from the received electron spin resonance signal. Moreover, the control portion 8 performs the processing of imaging the outside shape of the living body 7 from the received nuclear magnetic resonance signal. Lastly, the control portion 8 performs the processing of synthesizing the two images, and displays the synthesized image on the display portion 9.

Figure 3:
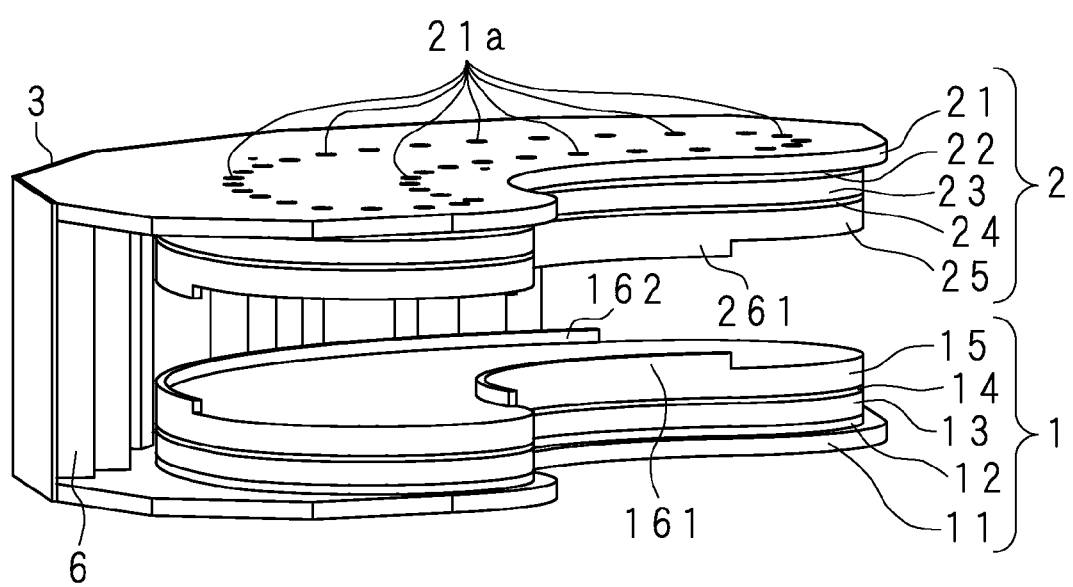
FIG. 3 is a schematic perspective view showing a first magnetic circuit.
Figure 4:
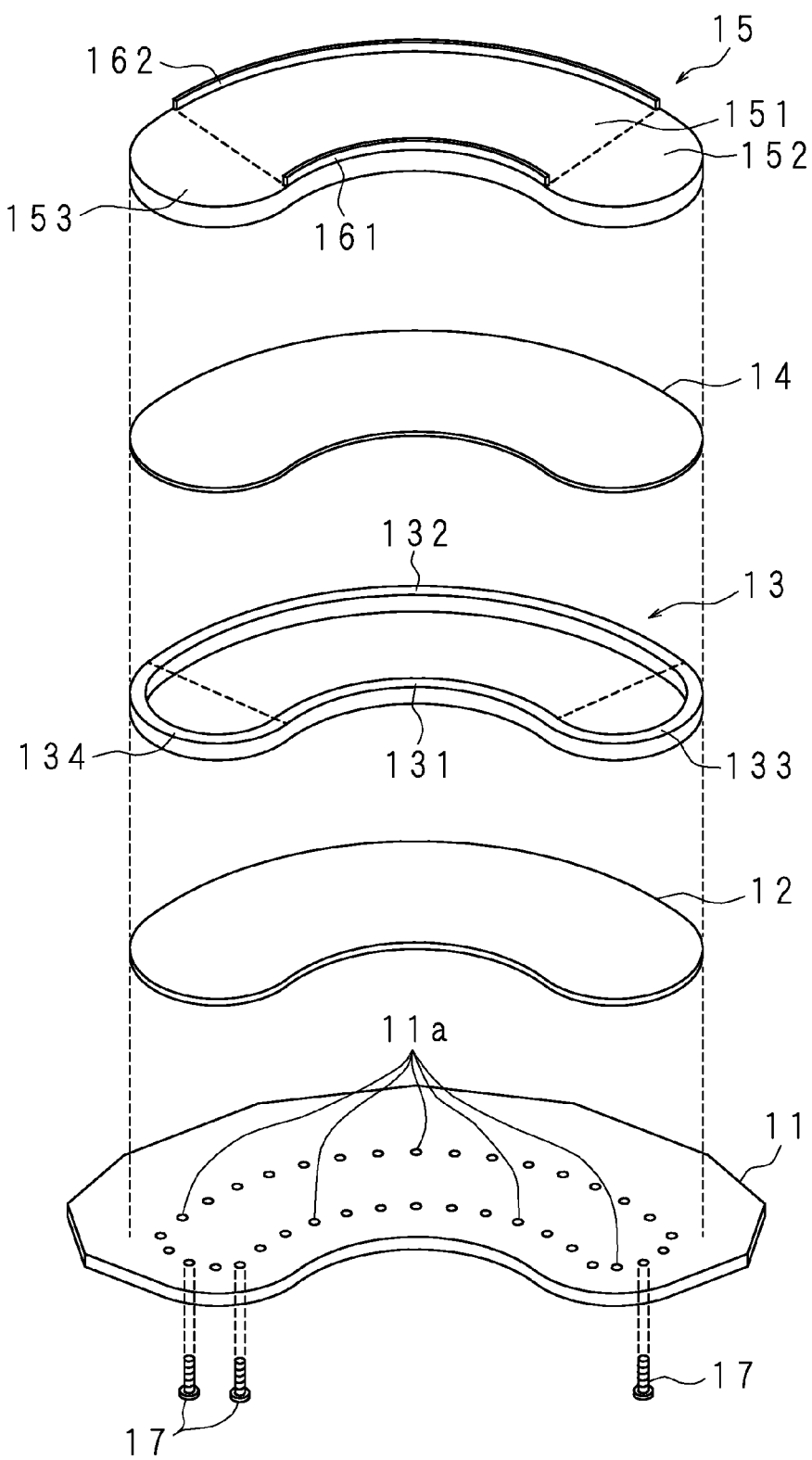
FIG. 4 is an exploded perspective view of a first magnetic pole.

The first magnetic circuit 10 will further be described. FIG. 3 is a schematic perspective view showing the first magnetic circuit 10. FIG. 4 is an exploded perspective view of the first magnetic pole 1. The first magnetic pole 1 is provided with the first yoke 11, a first non-magnetic plate 12, a first magnet 13, a first resin plate 14, a first magnetic pole piece 15, a first small diameter side protruding piece 161, and a first large diameter side protruding piece 162.

For the first yoke 11 of the first magnetic pole 1, for example, a silicon steel plate or iron is used, and the lower surface of the first yoke 11 is in contact with the upper surface of the mounting stand 4, which forms a horizontal surface. The first yoke 11 takes the form of a plate that is arc-shaped in planar view, and the outer rim on the large diameter side partly has a shape where a plurality of line segments are continuous while making obtuse angles with one another. The shape of the first yoke 11 is not specifically limited as long as the first yoke 11 is larger than the first magnet 13; for example, the outer rim on the large diameter side may be arc-shaped.

Figure 5:
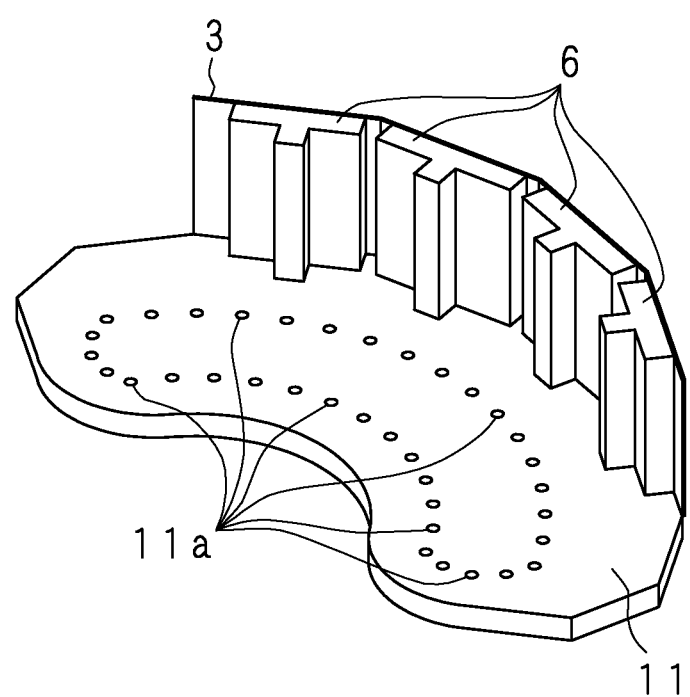
FIG. 5 is a schematic perspective view showing a first yoke, a back yoke and a support pillar.

FIG. 5 is a schematic perspective view showing the first yoke 11, the back yoke 3 and the support pillar 6. The plurality of line segments at the side portion of the first yoke 11 are coupled with the lower side surface on the small diameter side of the back yoke 3 formed of a plurality of flat plates coupled in the direction of the length, respectively. The upper side surface on the small diameter side of the back yoke 3 is coupled with the second yoke 21 described later.

On the upper surface on the large diameter side of the first yoke 11, a plurality of support pillars 6 that are convex in horizontal cross section and the upper ends of which supporting the second yoke 21 are provided along the back yoke 3. The upper surface on the small diameter side of the first yoke 11 is in contact with the lower surface of the first non-magnetic plate 12.

The outer shape of the first non-magnetic plate 12 has a plate form that is arc-shaped in planar view, and for example, a non-magnetic material such as austenitic stainless steel or aluminum is used.

Figure 6:
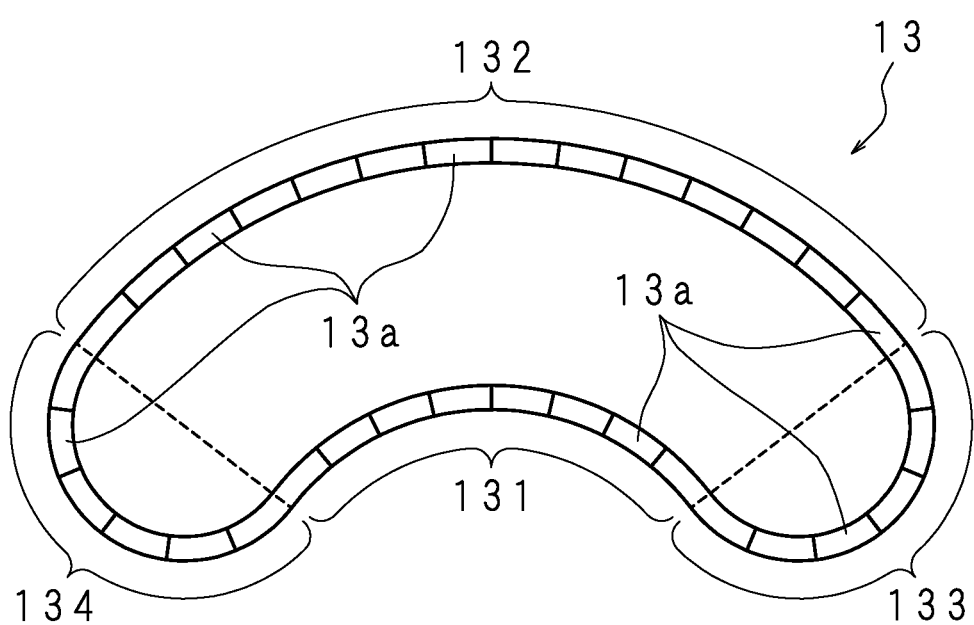
FIG. 6 is a schematic plan view of a first magnet.

The upper surface of the first non-magnetic plate 12 is in contact with the lower surface of the first magnet 13, the outer shape of which has a plate form that is arc-shaped in planar view similar to that of the first non-magnetic plate 12. FIG. 6 is a schematic plan view of the first magnet 13. The first magnet 13 includes a first small diameter side arc portion 131, a first large diameter side arc portion 132, a first one end side coupling arc portion 133 and a first other end side coupling arc portion 134.

The first small diameter side arc portion 131 and the first large diameter side arc portion 132 are concentric arcs of, for example, 110 degrees. The first one end side coupling arc portion 133 is, for example, semicircular arc, and couples the ends, close to the second magnetic circuit side 30, of the first small diameter side arc portion 131 and the first large diameter side arc portion 132. The first other end side coupling arc portion 134 is, for example, semicircular arc, and couples the ends, far from the second magnetic circuit side 30, of the first small diameter side arc portion 131 and the first large diameter side arc portion 132. The first one end side coupling arc portion 133 and the first other end side coupling arc portion 134 are not necessarily arc-shaped. For example, they may be linear and connect the first small diameter side arc portion 131 and the first large diameter side arc portion 132 or may be V-shaped.

The first magnet 13 is formed by arranging a plurality of block-form first small magnets 13a, 13a, . . . , 13a for which ferrite, neodymium magnet or the like is used. Therefore, the first magnet 13 has the form of an arc-shaped ring in planar view, and no magnets are provided inside the inner side surface. The first magnet 13 is capable of suppressing the difference in the strength of the magnetic field in the gap by such a structure.

The upper surface of the first magnet 13 is in contact with the lower surface of the first resin plate 14 having a plate form that is arc-shaped in planar view similar to that of the first non-magnetic plate 12 and for which, for example, fluorine resin or phenol resin is used. Moreover, the upper surface of the first resin plate 14 is in contact with the lower surface of the first magnetic pole piece 15 having a plate form that is arc-shaped in planar view similar to that of the first non-magnetic plate 12 and for which, for example, a silicon steel plate or iron is used.

Figure 7:
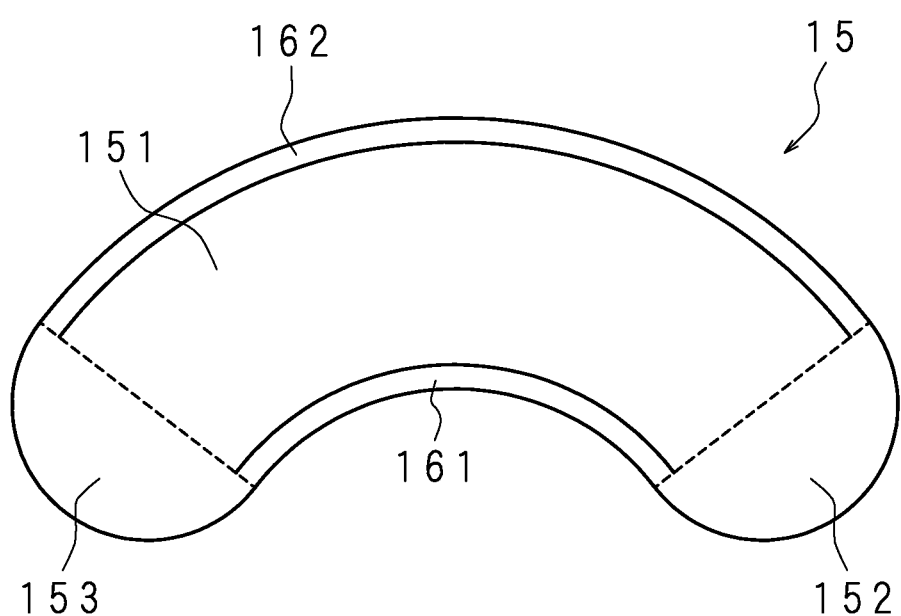
FIG. 7 is a schematic plan view showing a first magnetic pole piece.

FIG. 7 is a schematic plan view of the first magnetic pole piece 15. The first magnetic pole piece 15 includes a first central portion 151, a first one end side end portion 152 and a first other end side end portion 153. The first central portion is a portion forming an arc of, for example, 110 degrees, whereas the first one end side end portion 152 is a semicircular portion including the end close to the second magnetic circuit side 30 and the first other end side end portion 153 is a semicircular portion including the end far from the second magnetic circuit side 30.

To the outer rim on the small diameter side of the first central portion 151, the first small diameter side protruding piece 161 is fixed, and to the outer rim on the large diameter side of the first central portion 151, the first large diameter side protruding piece 162 is fixed. The first small diameter side protruding piece 161 and the first large diameter side protruding piece 162 for which, for example, a silicon steel plate or iron is used protrude upward. Because of the influences of, for example, the configuration of the first magnet 13 and the back yoke 3, a difference in magnetic field strength occurs between the small diameter side and the large diameter side. In order to reduce the difference in magnetic field strength between the small diameter side and the large diameter side, the first small diameter side protruding piece 161 is larger in protrusion amount than the first large diameter side protruding piece 162. It is only necessary that the first small diameter side protruding piece 161 be provided on part of the inner side of the first magnetic pole piece 15 and the first large diameter side protruding piece 162 be provided on part of the large diameter side of the first magnetic pole piece 15. For example, a structure may be adopted in which the first small diameter side protruding piece 161 is provided only on part of the small diameter side of the first central portion 151 or in which part thereof is provided on the first one end side end portion 152 or the first other end side end portion 153. The same applies to the first large diameter side protruding piece 162.

As described above, the first non-magnetic plate 12, the first magnet 13, the first resin plate 14 and the first magnetic pole piece 15 are substantially the same in outer shape, and are small in the area of the upper surface and lower surface compared with the first yoke 11. There are no restrictions to the shape of the first yoke 11 as long as the area of the upper surface and lower surface is larger than the area of the first non-magnetic plate 12, the first magnet 13, the first resin plate 14 and the first magnetic pole piece 15.

In the first yoke 11, first screw holes 11a, 11a, . . . , 11a passing through in positions similar to the arrangement of the first magnet 13 defined by the first small diameter side arc portion 131, the first large diameter side arc portion 132, the first one end side coupling arc portion 133 and the first other end side coupling arc portion 134 are provided. The first screw holes 11a, 11a, . . . , 11a are provided, for example, along a similar arc smaller than the inner side surface of the first magnet 13.

A ferromagnetic screw 17 for which iron, nickel or the like is used is screwed in the first screw hole 11a, whereby the magnetic field strength in the neighborhood of the first screw hole 11a changes. There are cases where the magnetic field strength of the first magnetic pole 1 is partly different from the strength planned at the time of design because of, for example, the usage environment, or the influence of deformation of the first magnet 13. In this case, by the screw(s) 17 being screwed in one or more than one first screw holes 11a from the lower surface side of the first yoke 11 as appropriate, the magnetic field strength is partly adjusted.

The shapes of the screw 17 and each first screw hole 11a are not specifically limited. Moreover, the first screw hole 11a may be an unthreaded hole, and in this case, instead of the screw 17, a rod-shaped object for which a ferromagnetic material is used is inserted in the hole. Moreover, non-through holes may be provided instead of the screw holes. The similar arc formed by the first screw holes 11a, 11a, . . . , 11a may be larger than the inner side surface of the first magnet 13.

Figure 8:
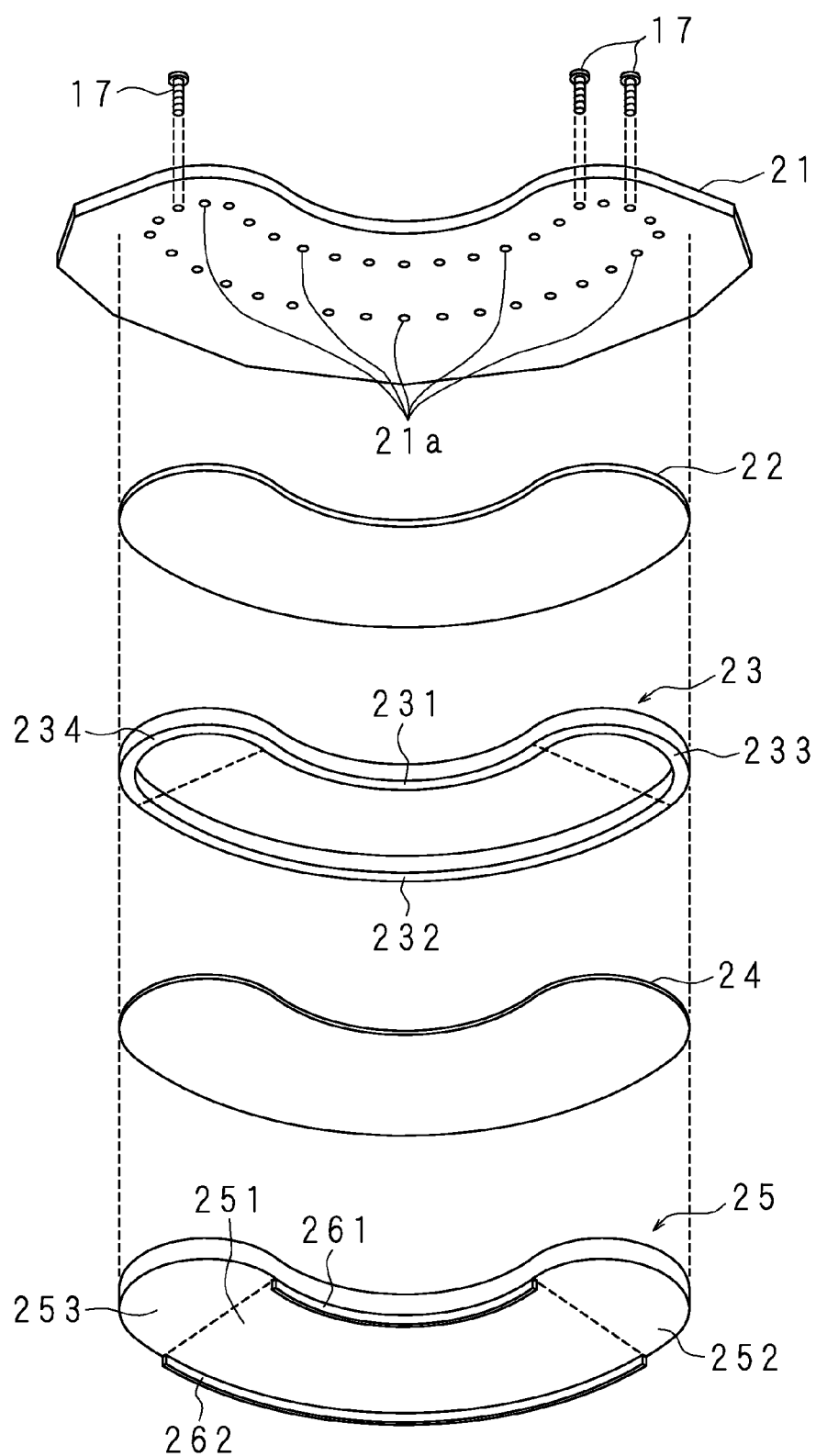
FIG. 8 is an exploded perspective view of a second magnetic pole.

FIG. 8 is an exploded perspective view of the second magnetic pole 2. The second magnetic pole 2 is provided with the second yoke 21, a second non-magnetic plate 22, a second magnet 23, a second resin plate 24, a second magnetic pole piece 25, a second small diameter side protruding piece 261 and a second large diameter side protruding piece 262.

The lower surface of the second yoke 21 having a shape plane-symmetric with the first yoke 11 and for which, for example, a silicon steel plate or iron is used is supported by the support plates 6, 6, . . . , 6. The plurality of line segments at the side portion of the second yoke 21 are coupled with the upper side surfaces on the small diameter side of the back yoke 3 formed of a plurality of flat plates coupled in the direction of the length, respectively.

The lower surface of the second yoke 21 is in contact with the upper surface of the second non-magnetic plate 22 having a shape plane-symmetric with the first non-magnetic plate 12 and for which a non-magnetic material such as aluminum or austenitic stainless steel is used.

The lower surface of the second non-magnetic plate 22 is in contact with the upper surface of the second magnet 23 having a shape plane-symmetric with the first magnet 13. The second magnet 23 includes a second small diameter side arc portion 231, a second large diameter side arc portion 232, a second one end side coupling arc portion 233 and a second other end side coupling arc portion 234. The second small diameter side arc portion 231 and the second large diameter side arc portion 232 are concentric arcs of, for example, 110 degrees. The second one end side coupling arc portion 233 is, for example, semicircular arc, and couples the ends, close to the second magnetic circuit 30, of the second small diameter side arc portion 231 and the second large diameter side arc portion 232. The second other end side coupling arc portion 234 is, for example, semicircular arc, and couples the ends, far from the second magnetic circuit 30, of the second small diameter side arc portion 231 and the second large diameter side arc portion 232. The second one end side coupling arc portion 233 and the second other end side coupling arc portion 234 are not necessarily arc-shaped; for example, they may be linear and connect the second small diameter side arc portion 231 and the second large diameter side arc portion 232 or may be V-shaped. The second magnet 23 is formed, like the first magnet 13, by arranging a plurality of block-form small magnets for which ferrite, neodymium magnet or the like is used.

The lower surface of the second magnet 23 is in contact with the upper surface of the resin-made second resin plate 24 having a shape plane-symmetric with the first resin plate 14. Moreover, the lower surface of the second resin plate 24 is in contact with the upper surface of the second magnetic pole piece 25 having a shape plane-symmetric with the first magnetic pole piece 15 and for which, for example, a silicon steel plate or iron is used.

To the outer rim on the small diameter side of a second central portion 251, the second small diameter side protruding piece 261 is fixed, and to the outer rim on the large diameter side of the second central portion 251, the second large diameter side protruding piece 262 is fixed. The second small diameter side protruding piece 261 and the second large diameter side protruding piece 262 for which a silicon steel plate, iron or the like is used protrude downward where the first magnetic pole 1 is disposed. The second small diameter side protruding piece 261 is larger in protrusion amount than the second large diameter side protruding piece 262. On the other hand, no protruding pieces are provided on a second one end side end portion 252 and a second other end side end portion 253. The first small diameter side protruding piece 161 is opposed to the second small diameter side protruding piece 261 with a gap in between and the first large diameter side protruding piece 162 is opposed to the second large diameter side protruding piece 262 with a gap in between. It is only necessary that the second small diameter side protruding piece 261 be provided on part of the inner side of the second magnetic pole piece 25 and the second large diameter side protruding piece 262 be provided on part of the large diameter side of the second magnetic pole piece 25. For example, a structure may be adopted in which the second small diameter side protruding piece 261 is provided only on part of the small diameter side of the second central portion 251 or in which part thereof is provided on the second one end side end portion 252 or the second other end side end portion 253. The same applies to the second large diameter side protruding piece 262.

As described above, the second non-magnetic plate 22, the second magnet 23, the second resin plate 24 and the second magnetic pole piece 25 are substantially the same in outer shape, and are smaller in the area of the upper surface and lower surface than the second yoke 21. There are no restrictions to the shape of the second yoke 21 as long as the area of the upper surface and lower surface is larger than the area of the second non-magnetic plate 22, the second magnet 23, the second resin plate 24 and the second magnetic pole piece 25.

In the second yoke 21, second screw holes 21a, 21a, . . . , 21a passing through in positions similar to the arrangement of the second magnet 23 defined by the second small diameter side arc portion 231, the second large diameter side arc portion 232, the second one end side coupling arc portion 233 and the second other end side coupling arc portion 234 are provided. The second screw holes 21a, 21a, . . . , 21a are provided, for example, along a similar arc smaller than the inner side surface of the second magnet 23.

Figure 9:
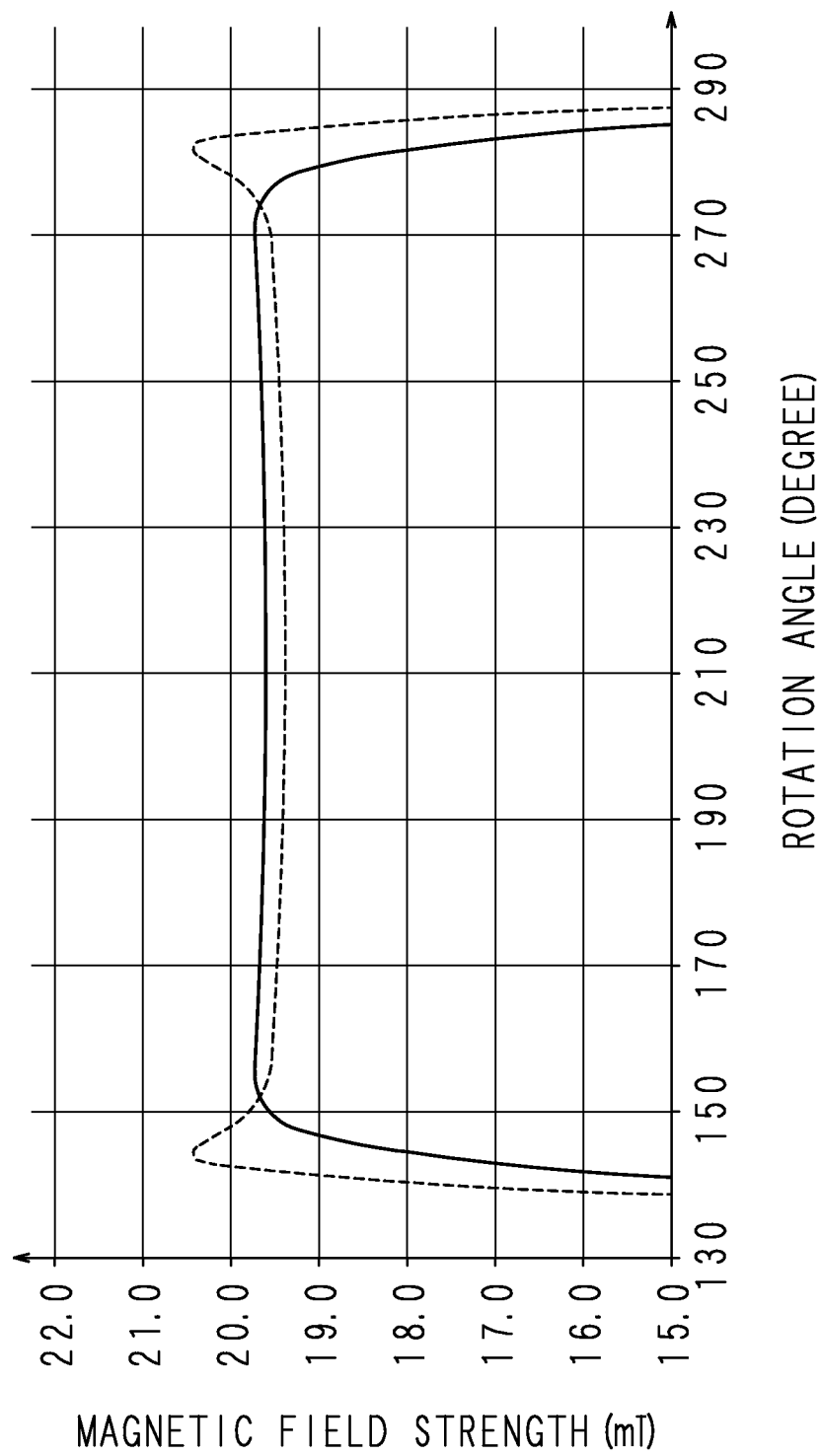
FIG. 9 is a graph showing the magnetic field strength in the first magnetic circuit.

Although the first small diameter side protruding piece 161, the first large diameter side protruding piece 162, the second small diameter side protruding piece 261 and the second large diameter side protruding piece 262 are pro-vided in order to increase the magnetic field strength in the neighborhood of the rim and increase a uniform magnetic field space, if they are provided on the entire rim, this conversely becomes a cause that makes the magnetic field nonuniform. FIG. 9 is a graph showing the magnetic field strength in the first magnetic circuit 10. The horizontal axis represents the rotation angle (degree) of the rotation shaft 43 from a predetermined position, and the vertical axis represents the magnetic field strength (mT). The broken line shows the magnetic field strength when the protruding piece is provided on the entire rims of the first magnetic pole piece 15 and the second magnetic pole piece 25. In this case, the first small diameter side protruding piece 161 and the first large diameter side protruding piece 162 are coupled together on the rim of the first magnetic pole piece 15, and the second small diameter side protruding piece 261 and the second large diameter side protruding piece 262 are coupled on the rim of the second magnetic pole piece 25. On the other hand, the solid line shows the magnetic field strength in the case of the present embodiment. In this case, the first small diameter side protruding piece 161 and the first large diameter side protruding piece 162 are provided only in the first central portion 151, and the second small diameter side protruding piece 261 and the second large diameter side protruding piece 262 are provided only in the second central portion 251.

As shown in FIG. 9, in the former case, parts where the magnetic field strength is very high are present in two positions at the neighborhood of 145 degrees and the neighborhood of 280 degrees. These two positions correspond to a position in the neighborhood between the first one end side coupling arc portion 133 and the second one end side coupling arc portion 233 and a position in the neighborhood between the first other end side coupling arc portion 134 and the second other end side coupling arc portion 234, respectively. On the other hand, in the latter case, there are no parts where the magnetic field strength is very high, and a uniform magnetic field space is maintained large.

Therefore, by providing the first small diameter side protruding piece 161 and the first large diameter side protruding piece 162 only on the rim of the first central portion 151 and providing the second small diameter side protruding piece 261 and the second large diameter side protruding piece 262 only on the rim of the second central portion 251, the uniform magnetic field space can be made large.

In order to adjust the magnetic field strength of the first magnetic circuit 10, one or both of the first non-magnetic plate 12 and the second non-magnetic plate 22 may be replaced with a non-magnetic plate of a different thickness.

According to the present embodiment, since the first magnet 13 and the second magnet 23 constituting the first magnetic circuit 10 are arc-shaped in planar view, the first magnetic circuit 10 can apply a magnetic field for a long time.

Second Embodiment

Figure 10:
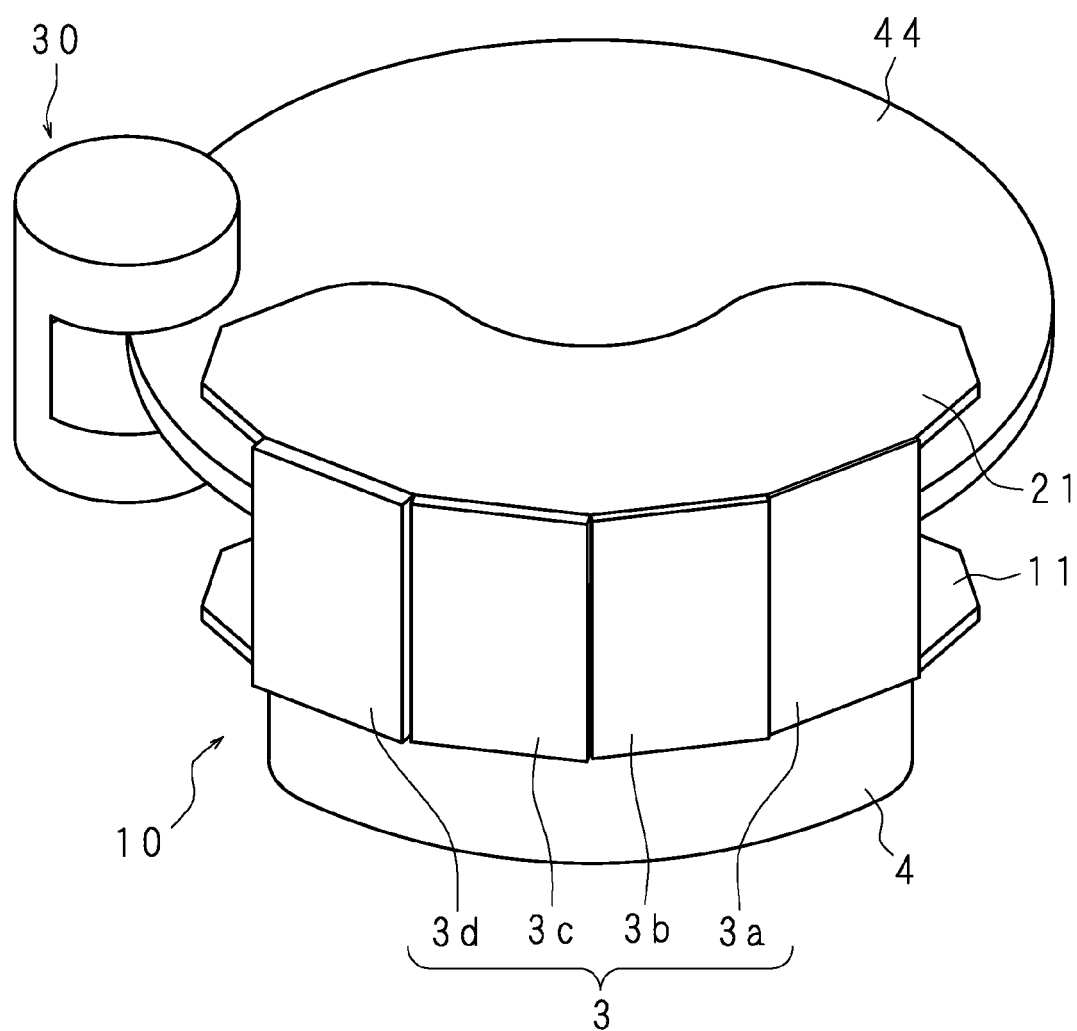
FIG. 10 is a schematic perspective view showing the back yoke.

The second embodiment will be described. The present embodiment relates to a mode where the thickness of the back yoke 3 differs according to the position. FIG. 10 is a schematic perspective view showing the back yoke 3. In the back yoke 3 according to the present embodiment, the thickness of one end side which is the side close to the second magnetic circuit 30 is larger than that of the other end side. The flat plates 3a to 3d constituting the back yoke 3 are structured so that the closer they are to the second magnetic circuit 30, the larger the thickness is. That is, the thickness of the flat plates constituting the back yoke 3 is increased in the order of the flat plates 3a, 3b, 3c and 3d.

To generate nuclear magnetic resonance, a magnetic field stronger than that to generate electron spin resonance is required. Therefore, the magnetic field generated by the second magnetic circuit 30 is stronger than the magnetic field generated by the first magnetic circuit 10. However, for this reason, in the neighborhood of the end, on the side of the second magnetic circuit 30, of the first magnetic circuit 10, the uniform magnetic field space formed by the first magnetic circuit 10 is sometimes impaired because of the influence of the magnetic field leaking from the second magnetic circuit 30.

Figure 11:
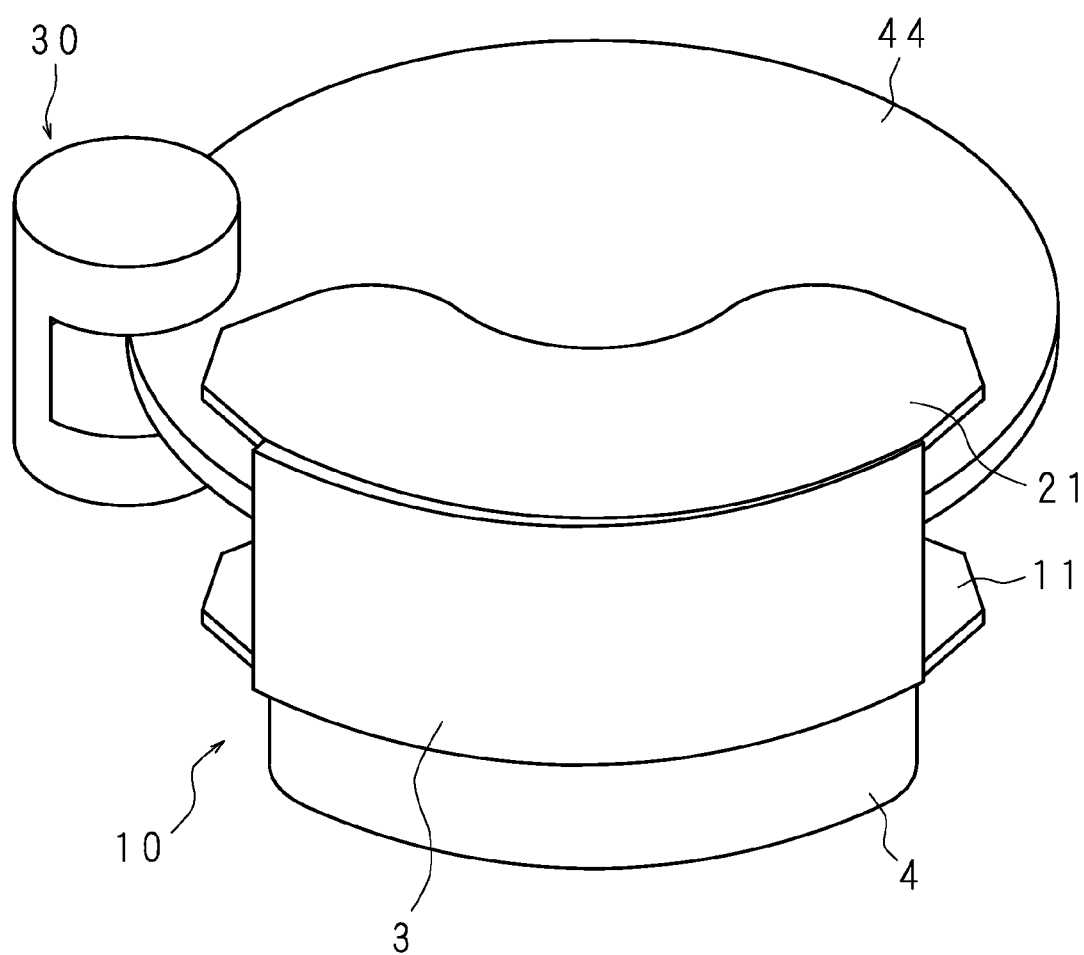
FIG. 11 is a schematic perspective view showing another example of the back yoke.

According to the present embodiment, by making thick the end on the one end side of the back yoke 3, the influence of the magnetic field leaking from the second magnetic circuit 30 can be suppressed. The back yoke 3 may be formed of one or more than one curved plates. FIG. 11 is a schematic perspective view showing another example of the back yoke 3. In such an example, the back yoke 3 is formed of one curved plate, and is structured so that the closer it is to the second magnetic circuit 30, the thicker the back yoke 3 is.

Third Embodiment

Figure 12:
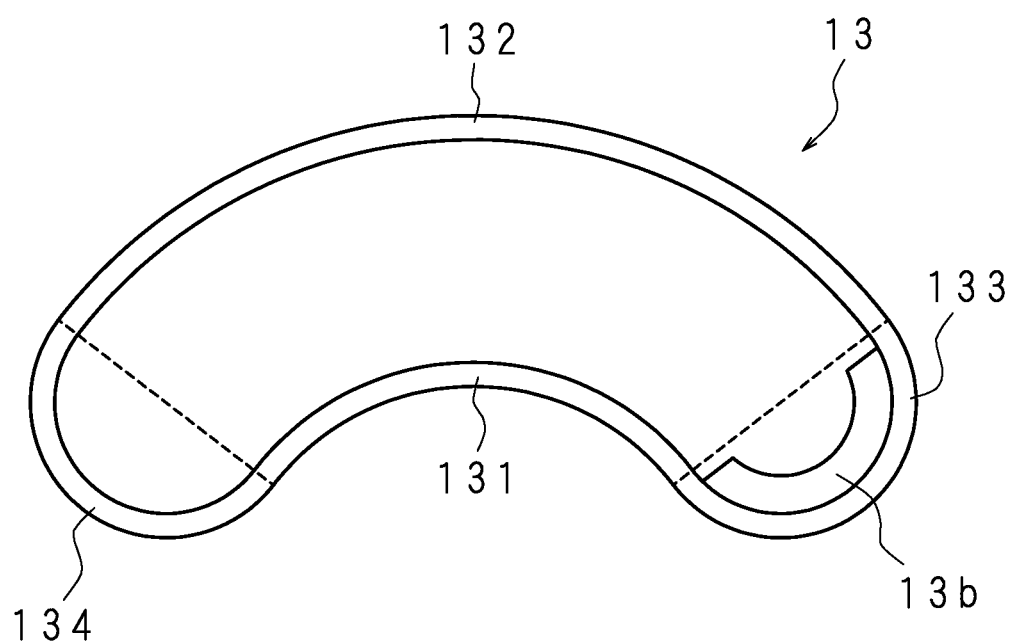
FIG. 12 is a schematic plan view showing an example where an auxiliary magnet is provided to the first magnet.
Figure 13:
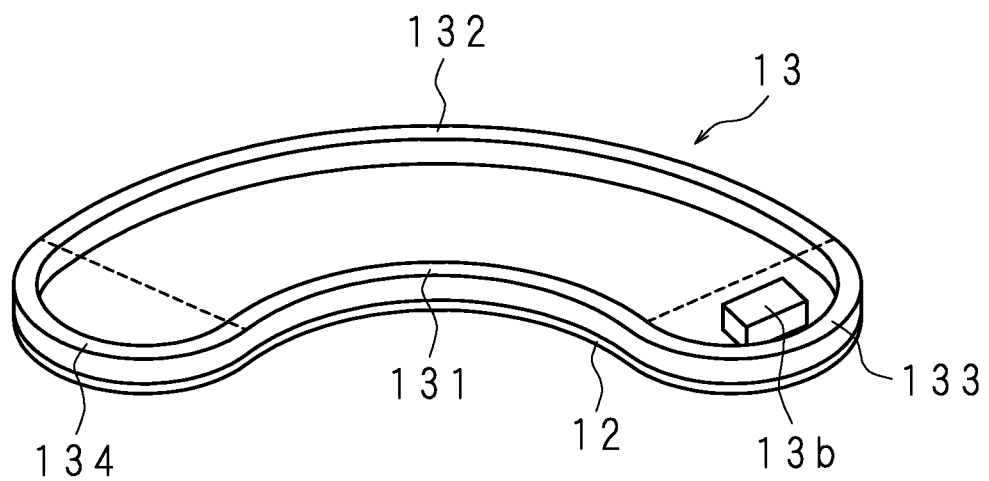
FIG. 13 is a schematic perspective view showing another example where the auxiliary magnet is provided to the first magnet.

The third embodiment will be described. The present embodiment relates to a mode where a magnet is further added. FIG. 12 is a schematic plan view showing an example where a first auxiliary magnet 13b is provided to the first magnet 13. As shown in FIG. 12, the first auxiliary magnet 13b is fixed to the inside of the first one end side coupling arc portion 133. Thereby, the first auxiliary magnet 13b plays a role in increasing the magnetic field strength of the end, on the side of the second magnetic circuit 30, of the first magnetic circuit 10 and assisting the uniformalization of the magnetic field in a predetermined space. Likewise, the second magnet 23 may be provided with an auxiliary magnet fixed to the second one end side coupling arc portion 233. Moreover, FIG. 13 is a schematic perspective view showing another example where the first auxiliary magnet 13b is provided to the first magnet 13. The first auxiliary magnet 13b is not necessarily fixed to the first one end side coupling arc portion 133; for example, it may be attached to the first magnet 13 in the form of being mounted on the first non-magnetic plate 12 on the one end side.

According to the present embodiment, since the first auxiliary magnet 13b can increase the magnetic field strength at the end on the side of the second magnetic circuit 30, the above-mentioned influence of the magnetic field by the second magnetic circuit 30 can be suppressed.

The embodiments disclosed herein should be considered as illustrative in all respects and not restrictive. The scope of the present invention is defined not by the meaning described above but by the claims, and it is intended that all changes that fall within the meaning and scope equivalent to the claims are embraced.

The invention claimed is:

1. A magnetic circuit comprising:
two arc-shaped ring magnets comprising no magnet portions in inner surfaces thereof and disposed so as to be opposed to each other; and
two arc-shaped yokes disposed so as to be opposed to each other in a same direction as the two arc-shaped ring magnets with the two arc-shaped ring magnets interposed between the yokes.

2. The magnetic circuit according to claim 1, wherein
the two arc-shaped ring magnets are formed by arranging a plurality of small magnets along a large diameter side arc portion, along a small diameter side arc portion and along coupling portions coupling ends of the two arc portions.

3. The magnetic circuit according to claim 1, further comprising:
two arc-shaped magnetic pole pieces disposed between the two arc-shaped ring magnets in the same direction as the two arc-shaped ring magnets; and
one or more protruding pieces provided on an outer rim of each of the magnetic pole pieces and protruding toward the other magnetic pole piece.

4. The magnetic circuit according to claim 3, wherein
the protruding pieces include:
one or more large diameter side protruding pieces located on a large diameter side of the magnetic pole piece(s); and
one or more small diameter side protruding pieces located on a small diameter side of the magnetic pole piece(s).

5. The magnetic circuit according to claim 2, wherein
the yokes include a plurality of hole portions along an arc similar to outer rims of the arc-shaped ring magnets.

6. The magnetic circuit according claim 1, further comprising
a plate-like auxiliary yoke that couples the two yokes.

7. The magnetic circuit according to claim 6, wherein
the auxiliary yoke is provided along outer rims on the large diameter side of the two yokes and one end side in a direction of a length is thicker than the other end side.

8. The magnetic circuit according to claim 2, further comprising
one or more auxiliary magnets attached to the arc-shaped ring magnets.

9. The magnetic circuit according to claim 8, wherein
one or more auxiliary magnets are fixed to one end side of the two arc-shaped ring magnets which is an inside of one or more coupling portions.

10. The magnetic circuit according to claim 1, further comprising:
two non-magnetic plates,
one of the two non-magnetic plates being located between one of the two arc-shaped ring magnets and one of the two yokes facing the one of the two arc-shaped ring magnets, and the other one of the two non-magnetic plates being located between the other one of the two arc-shaped ring magnets and the other one of the two yokes facing the other one of the two arc-shaped ring magnet.

11. The magnetic circuit according to claim 5, further comprising a ferromagnetic screw in one or more of the hole portions of the yokes.

12. The magnetic circuit according to claim 6, further comprising one or more support pillars provided along the auxiliary yoke.

* * * * *